(12) United States Patent
Maxton et al.

(10) Patent No.: US 9,743,574 B1
(45) Date of Patent: Aug. 29, 2017

(54) MOBILE SOIL OPTICAL MAPPING SYSTEM

(75) Inventors: Chase Maxton, Salina, KS (US); Paul Drummond, Minneapolis, KS (US); Eric Lund, Salina, KS (US); Kyle Jensen, Salina, KS (US)

(73) Assignee: Veris Technologies, Inc., Salina, KS (US)

( * ) Notice: Subject to any disclaimer, the term of this patent is extended or adjusted under 35 U.S.C. 154(b) by 1133 days.

(21) Appl. No.: 13/277,208

(22) Filed: Oct. 19, 2011

Related U.S. Application Data (63) Continuation-in-part of application No. 12/253,594, filed on Oct. 17, 2008, now Pat. No. 8,204,689.

(60) Provisional application No. 61/394,740, filed on Oct. 19, 2010, provisional application No. 60/982,395, filed on Oct. 24, 2007.

(51) Int. Cl.
| | |
|---|---|
| *G01V 3/38* | (2006.01) |
| *G01N 31/00* | (2006.01) |
| *A01B 79/00* | (2006.01) |
| *G01S 17/89* | (2006.01) |
| *G01N 21/31* | (2006.01) |
| *G01N 21/3563* | (2014.01) |

(52) U.S. Cl.
CPC ........... *A01B 79/005* (2013.01); *G01N 21/31* (2013.01); *G01N 21/3563* (2013.01); *G01S 17/89* (2013.01)

(58) Field of Classification Search
CPC .... G01S 17/89; G01N 21/31; G01N 21/3563; G01N 21/359
USPC ....................................................... 702/5, 28
See application file for complete search history.

(56) References Cited

U.S. PATENT DOCUMENTS

| | | | |
|---|---|---|---|
| 5,038,040 A * | 8/1991 | Funk et al. | 250/339.02 |
| 5,044,756 A | 9/1991 | Gaultney | |
| 5,621,669 A * | 4/1997 | Bjornsson | A01G 25/167 239/63 |
| 6,356,830 B1 | 3/2002 | Adamchuck et al. | |
| 6,393,927 B1 | 5/2002 | Biggs et al. | |
| 6,608,672 B1 | 8/2003 | Shibusawa | |
| 6,855,933 B2 | 2/2005 | Stone et al. | |

(Continued)

OTHER PUBLICATIONS

"Things You Should Know About LED's and Photodiodes", Oct. 2007.*

(Continued)

*Primary Examiner* — Michael Nghiem
(74) *Attorney, Agent, or Firm* — Jeffrey L. Thompson; Thompson & Thompson, P.A.

(57) ABSTRACT

A soil mapping system for collecting and mapping soil reflectance data in a field includes an implement having a furrow opener for creating a furrow and an optical module. The optical module is arranged to collect soil reflectance data at a predetermined depth within the furrow as the implement traverses a field. The optical module includes two monochromatic light sources, a window arranged to press against the soil, and a photodiode for receiving light reflected back from the soil through the window. The two light sources have different wavelengths and are modulated at different frequencies. The photodiode provides a modulated voltage output signal that contains reflectance data from both of the light sources. Additional measurement devices are carried by the implement for collecting additional soil property data, such as electrical conductivity, pH, and elevation, which can be used together with the optical data to determine variations in soil organic matter.

13 Claims, 7 Drawing Sheets

(56) References Cited

U.S. PATENT DOCUMENTS

| | | | |
|---|---|---|---|
| 7,216,555 B2 | 5/2007 | Drummond et al. | |
| 7,708,145 B2 | 5/2010 | Li et al. | |
| 8,204,689 B2* | 6/2012 | Christy et al. | 702/5 |
| 2002/0039186 A1* | 4/2002 | Rosenberg | 356/432 |
| 2002/0131046 A1* | 9/2002 | Christy | G01N 21/15 |
| | | | 356/445 |
| 2004/0206282 A1* | 10/2004 | Sandoval et al. | 111/52 |
| 2005/0172733 A1* | 8/2005 | Drummond et al. | 73/864.41 |
| 2006/0146971 A1* | 7/2006 | Kaizuka | 375/376 |
| 2008/0291455 A1* | 11/2008 | Holland | 356/445 |
| 2009/0112475 A1 | 4/2009 | Christy et al. | |
| 2010/0180695 A1* | 7/2010 | Sauder et al. | 73/862.045 |

OTHER PUBLICATIONS

Document Properties/Date for "Things You Should Know About LED's and Photodiodes", Oct. 2007.*
Adamchuk et al., "On-the-go soil sensors for precision agrigulture", Jun. 12, 2004.*
Definition of Watt/Parallel Linkage, Mar. 2015.*

\* cited by examiner

MOBILE SOIL OPTICAL MAPPING SYSTEM

RELATED APPLICATIONS

This application claims priority of U.S. Provisional Application No. 61/394,740 filed on Oct. 19, 2010. This application is a continuation-in-part of U.S. application Ser. No. 12/253,594 filed on Oct. 17, 2008, now U.S. Pat. No. 8,204,689, which claims priority of U.S. Provisional Application No. 60/982,395 filed on Oct. 24, 2007. The entire contents of these prior applications are incorporated herein by reference.

BACKGROUND OF THE INVENTION

Field of the Invention

The present invention relates generally to methods and devices for analyzing and mapping soil properties within a field. In particular, the present invention relates to methods and devices for collecting and mapping soil reflectance data on-the-go.

Description of the Related Art

Variations in soil properties can be detected, even with the human eye, based on differences in light reflectance. Darker soils contain higher levels of moisture or organic matter than light-colored soils. Molecules containing C—H, O—H, or N—H bonds that are exposed to light vibrate due to the force of the electric field. This vibration absorbs optical energy so that less light is reflected off the soil. While this can be detected visually, light sensors, especially those in the near infrared (NIR), can quantify the reflectance characteristics and provide the data needed to develop calibrations to soil properties. Soil reflectance has been studied extensively since the 1970s and is widely reported in the scientific literature as an effective means for approximating soil organic matter and carbon. There have been some uses of bare soil photographs where the darker areas were correlated with higher organic matter levels, but with the increased use of conservation tillage and no-till farming, the ability to collect such images has diminished. Rudimentary devices to collect reflectance data in the field, operating near or under the soil surface, were mobilized in the early 1990s. Due to several limitations in their designs, neither of these was fully commercialized.

Since the advent of GPS-enabled precision farming in the mid-1990s, growers have sought ways to better delineate areas of contrasting productivity within their fields. Yield maps produced by combine yield monitors and remote crop imagery both show annual crop differences, but relating those temporal variations to fundamental productivity zones has proven challenging due to the many factors affecting crop growth. Soil surveys produced by the USDA have also been examined, but the scale at which these were created is too coarse to show many important inclusions of varying soils. On-the-go sensors to measure other soil properties have been developed and widely commercialized, including one that measures soil pH, and several that relate soil electrical conductivity measurements to soil texture and soil salinity. These proximal sensors collect dense datasets and their widespread use has generated an awareness of soil spatially variability within fields. None of these commercial sensors measures soil organic matter consistently.

Organic matter is an important factor in crop growth, as it affects soil moisture infiltration and retention, soil tilth, rooting depth, soil-applied herbicide activity, nitrogen release, and other aspects of nutrient cycling. A precise map of organic matter will provide growers with an important piece of information as they seek to vary nitrogen, seed population, herbicides, and other inputs.

Veris Technologies Inc., the assignee of the present application, began development of soil optical devices in 2002 and has described a commercialized spectrophotometer system for mapping soil in its U.S. Patent Publication No. 2009-0112475 (Christy et al.). That system includes a field-deployed implement containing costly visible and near-infrared spectrometers, which collect spectra that include over 300 individual wavelengths. That level of technology is needed in soil research and where carbon measurements require an extremely high level of precision, but is not practical for grower and consultant use due to expense and complexity.

There is a need in the industry for a mapping system suitable for grower and consultant use, which is capable of providing accurate, useful soil organic matter measurements using a simple, low cost design.

SUMMARY OF THE INVENTION

A soil mapping system for collecting and mapping soil reflectance data in a field includes an implement having a row unit with a furrow opener for creating a furrow and an optical module. The optical module is arranged to collect soil reflectance data at a predetermined depth within the furrow as the implement traverses a field. An opening coulter and a pair of trash clearing disks can be used to clear residue and cut a slice in front of the furrow opener. The furrow opener in one embodiment comprises two disks operating at a slight angle relative to the direction of travel to form a V-shaped slot in the soil, similar to double disk furrow opener used in a row unit of an agricultural planter. Gauge wheels can be positioned on each side of the furrow opener disks to maintain a consistent furrow depth and to scrape soil from the outer sidewall of the disk during operation. The row unit is connected to a tool bar by a parallel linkage, which allows the furrow opener and optical module to follow ground undulations. An adjustable down-force feature allows the row unit to be adjusted to match soil conditions. Closing wheels or closing disks are provided to close the furrow behind the optical module to prevent erosion.

The optical module includes two monochromatic light sources, a sapphire window arranged to press against the soil, and a single photodiode for receiving light reflected back from the soil through the window. The two light sources have different wavelengths and are modulated at different frequencies by a function generator contained in a controller. The photodiode provides a modulated voltage output signal that contains reflectance data from both of the light sources. The output signal from the photodiode is conditioned, converted to digital, and output as optical data to a data logger or PC. Additional measurement devices are carried by the implement for collecting additional soil property data, such as electrical conductivity, pH, and elevation, which can be used together with the optical data to determine variations in soil organic matter. A GPS signal is used to georeference all of the data.

According to one aspect of the present invention, a soil mapping system is provided, comprising: an implement for traversing a field to be mapped: a furrow opener on the implement for creating a furrow as the implement traverses a field; and an optical module on the implement. The optical module comprises at least one light source, a window arranged to press against soil at a predetermined depth within the furrow with consistent pressure to provide a self-cleaning function, and a photodiode for receiving light reflected back from the soil through the window.

According to another aspect of the present invention, a soil mapping system is provided, comprising: an implement for traversing a field to be mapped; an optical module carried by the implement for collecting soil reflectance data from soil in the field; and at least one additional measurement device carried by the implement for collecting data for at least one soil property that relates to soil organic matter. The additional measurement device is selected from the group consisting of an electrical conductivity measurement device, an on-the-go soil pH measuring device, and an elevation measuring device. A means is also provided for georeferencing data collected by the optical module and the additional measurement device According to another aspect of the present invention, an optical module is provided for a soil mapping system, the optical module comprising: two monochromatic light sources having different wavelengths which are modulated at different frequencies; a window having an outside surface adapted to be pressed against soil; and a photodiode arranged to receive light from the two light sources which is reflected back from the soil through the window. The photodiode having an output signal comprising a modulated voltage that contains soil reflectance data from both of the light sources.

Numerous other objects of the present invention will be apparent to those skilled in this art from the following description wherein there is shown and described an embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

A mobile soil mapping system for collecting on-the-go reflectance measurements of soil in a field according to the present invention will now be described in detail with reference to FIGS. 1 to 13 of the accompanying drawings.

The primary objective of the present invention is to collect on-the-go optical measurements and correlate the data with soil organic matter levels. The soil mapping system described herein minimizes interferences from soil moisture and other sources of error through its mechanical, electronic, and data processing innovations.

Collecting high-quality optical measurements of soil in situ requires preparing the soil scene so the sensor will have an ideal view of the soil. This is accomplished in part by maintaining a consistent depth in the soil. The consistent depth is important because simple optical devices have difficulty differentiating soil moisture from organic matter, and soil moisture varies much more widely with depth than does organic matter. If the measurements are collected from a soil-engaging device that is bouncing over the field, the resulting data will be responding to moisture variations much more than if the measurements are at a consistent depth.

It is also important that the measurement scene be free of dust, crop residue, or mud that may adhere to the sensor. Therefore, the measurement window on the optical module should be kept clean. If soil from another part of the field remains on the window, the system would erroneously georeference the soil variations in the field.

FIGS. 1 to 5 illustrate an implement 10 having a frame with a toolbar 17 supported above the soil by frame support wheels, and a specially configured row unit 11 used to collect optical measurements of soil according to the present invention. The row unit 11 includes a pair of trash clearing wheels 12 for removing residue, a coulter 13 for cutting through any remaining residue and for opening a slot in the soil, a furrow opener assembly 14 that creates a furrow in the soil, and an optical module 15 having a window 16 arranged to be pressed against the soil at a predetermined depth within the furrow. The row unit 11 can be mounted to the toolbar 17 of the implement 10 by a parallel linkage 18 that allows the furrow opener 14 and optical module 15 to follow ground undulations while maintaining a consistent depth in the soil. A plurality of springs 19 or a pneumatic system (not shown) can be used to provide an adjustable down-force to match soil conditions.

Figure 1:
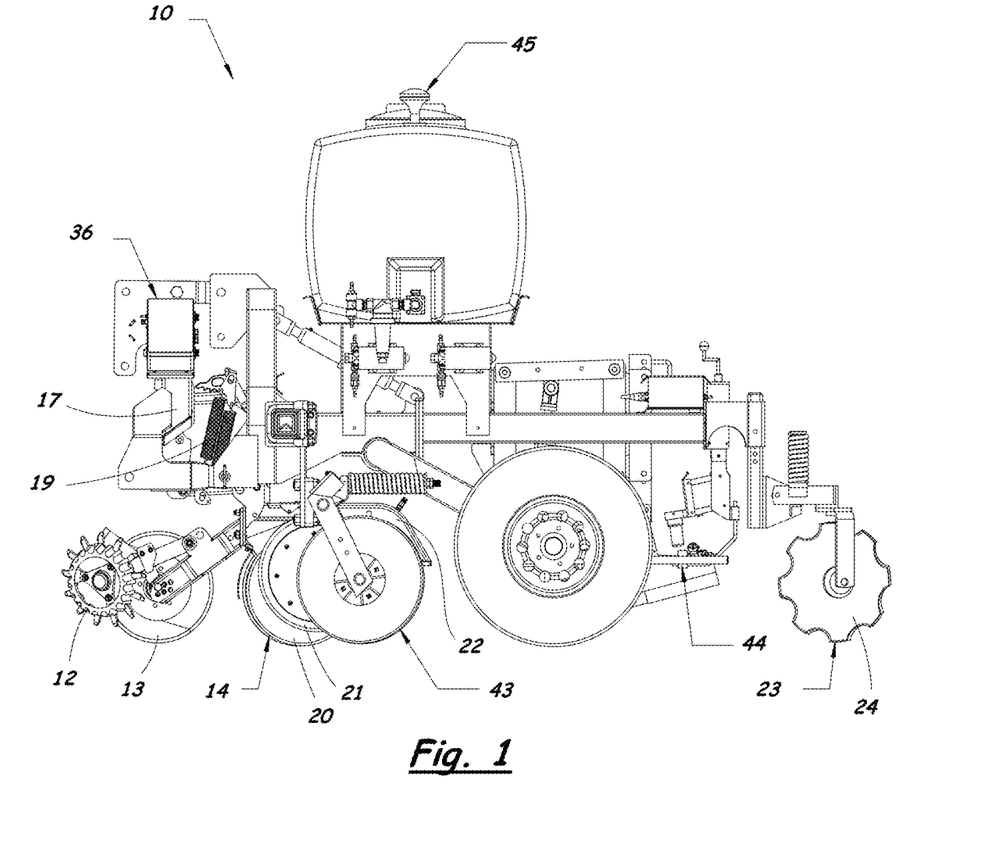
FIG. 1 is an elevation view of a mobile soil mapping system according to the present invention.
Figure 2:
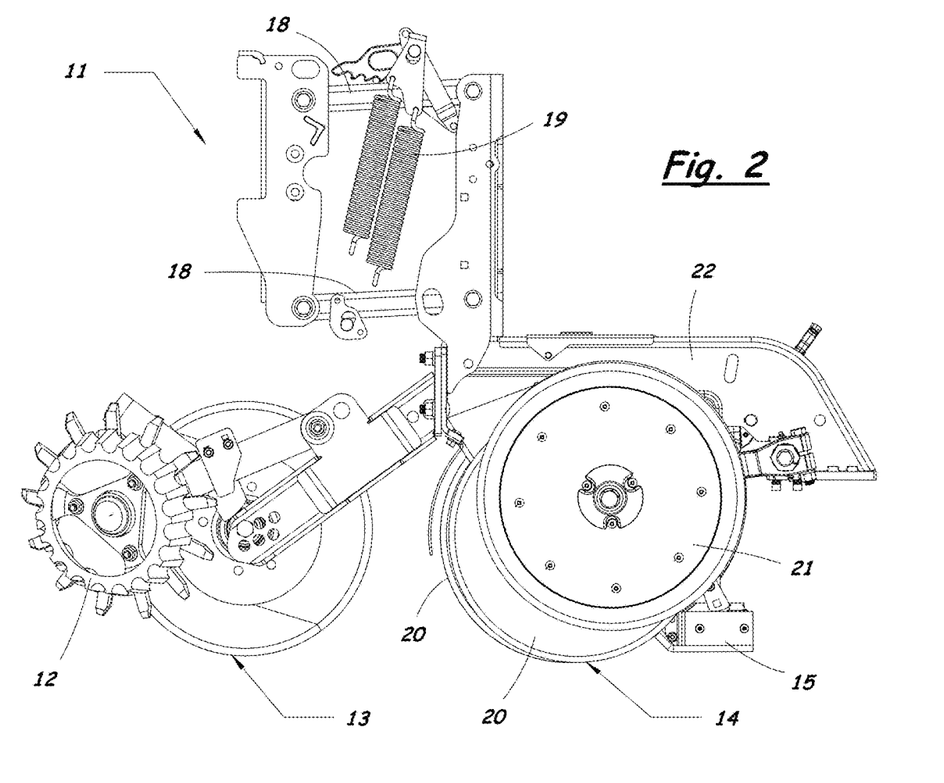
FIG. 2 is an elevation view of a row unit for an optical module of the soil mapping system shown in FIG. 1.

The furrow opener 14 in the illustrated embodiment includes two disks 20 that penetrate and follow in the slot created by the leading coulter 13. The disks 20 are arranged at a slight angle relative to a direction of travel so as to form a V-shaped slot or furrow in the soil. For example, the furrow opener 14 can be constructed in the same manner as a conventional double disk furrow opener used in an agricultural planter. Other types of furrow openers may also be used with the present invention.

The optical module 15 is mounted between the two furrow opener disks 20 and is kept at a constant depth in the soil by being pressed against the bottom of the furrow while measurements are being made. The consistent pressure of the optical module 15 against the soil provides a self cleaning function that prevents a buildup of soil on the window 16 of the optical module 15.

A pair of gauge wheels 21 are mounted in close proximity to the furrow opener disks 20 to control the operating depth of the disks 20 and to scrape off any soil that adheres to the outer surfaces of the disks 20 during operation. The gauge wheels 21 are mounted together with the furrow opener disks 20 and the optical module 15 on a subframe 22 of the row unit 11. The gauge wheels 21 maintain a consistent depth of operation of the optical module 15 in the soil during operation. For example, the gauge wheels 21 can be adjusted relative to the furrow opener disks 20 and optical module 15 to allow measurements to be taken at selected depths of approximately 1 to 3 inches below the soil surface.

Figure 3:
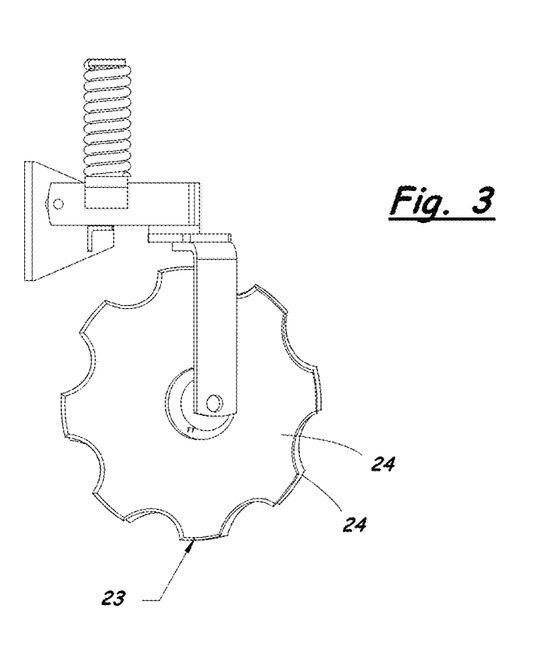
FIG. 3 is an elevation view of a closing disk assembly used in the soil mapping system shown in FIG. 1.
Figure 4:
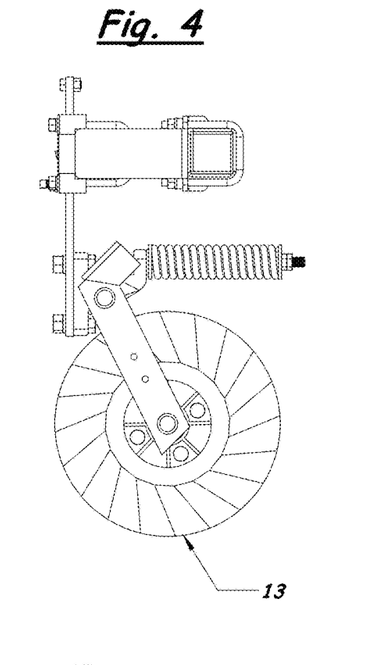
FIG. 4 is an elevation view of a coulter assembly used for slicing soil and residue in front of the furrow opener assembly for the optical module.
Figure 5:
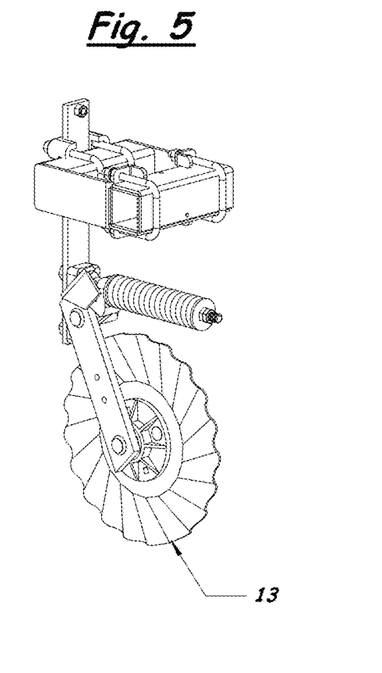
FIG. 5 is a perspective view of the coulter assembly shown in FIG. 4.

A furrow closing assembly 23 follows along behind the optical module 15 to close the furrow after optical measurements are taken to prevent erosion. The furrow closing assembly 23 can be a pair of closing disks 24 as shown in FIGS. 1 and 3, or a pair of closing wheels 25 as shown in FIGS. 8 to 13.

Figure 6:
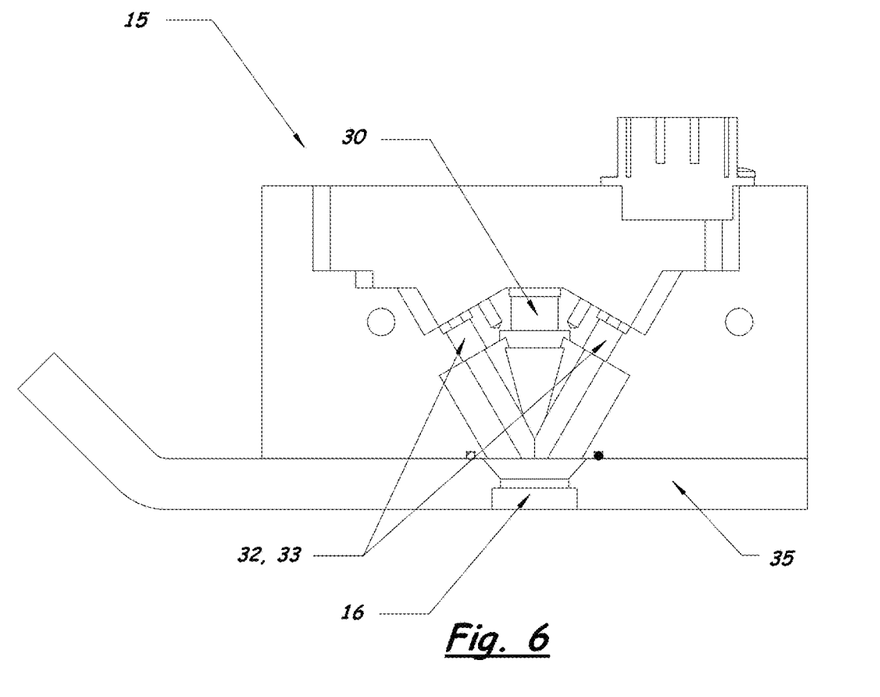
FIG. 6 is a detail view of an optical module used in the soil mapping system.
Figure 7:
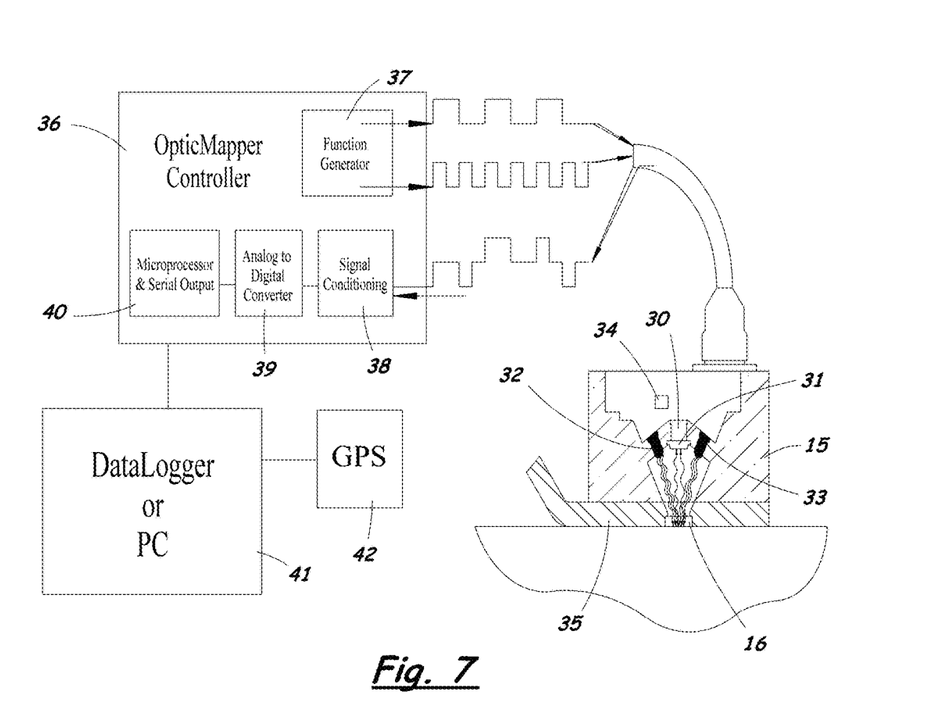
FIG. 7 is a schematic view of the optical module and controller for collecting reflectance data from the soil.
Figure 8:
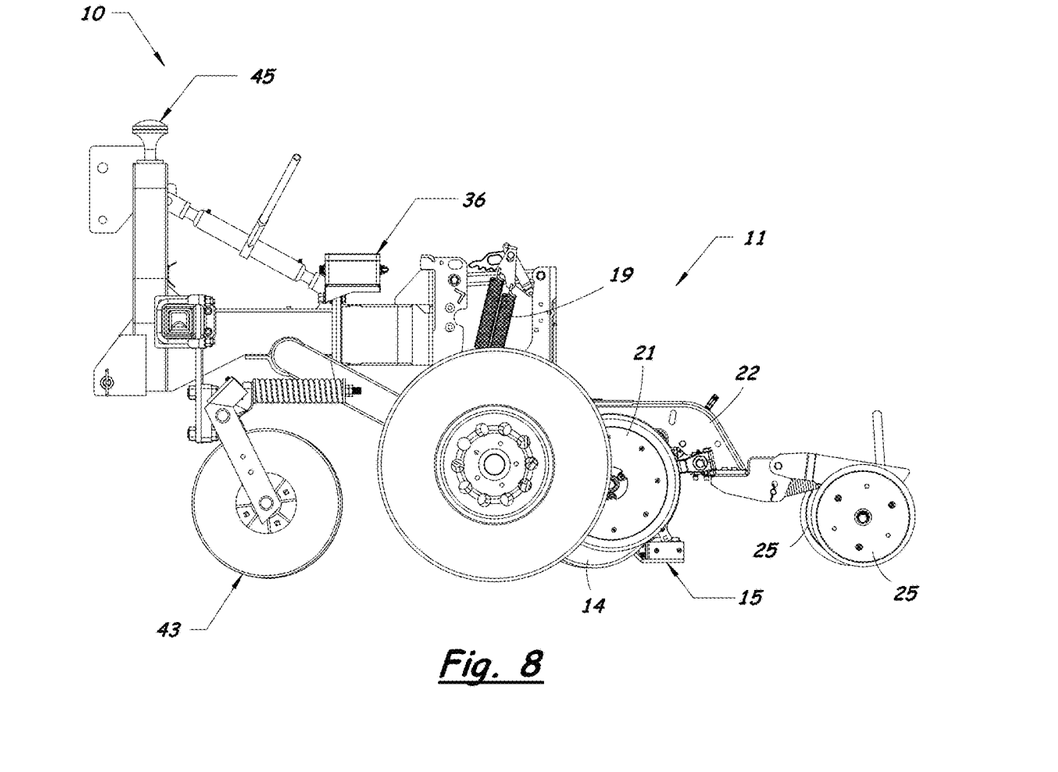
FIG. 8 is an elevation view of a mobile soil mapping system according to another embodiment of the present invention.
Figure 9:
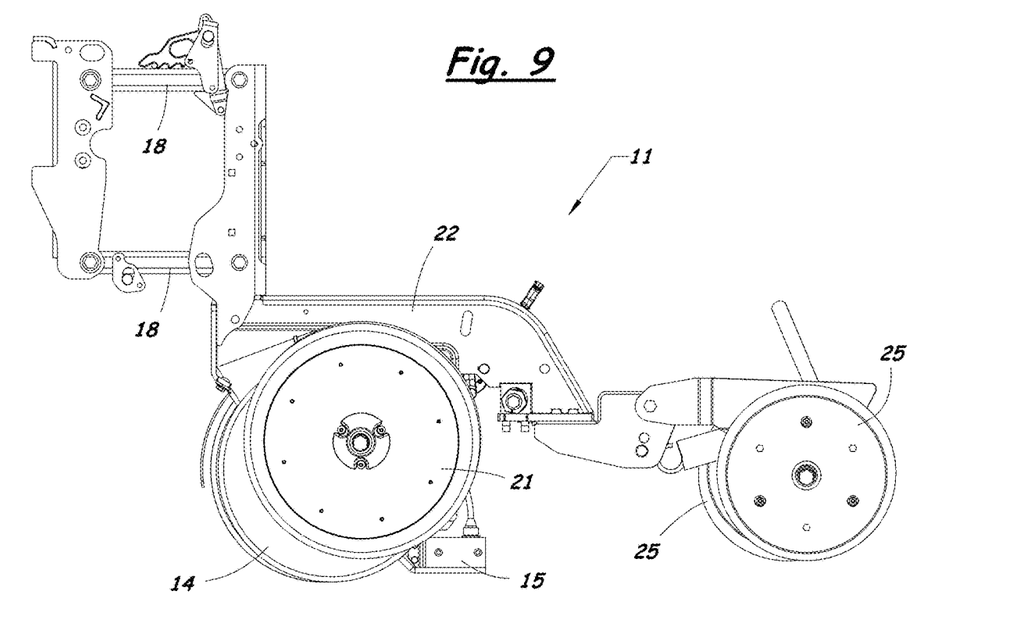
FIG. 9 is an elevation view of a row unit for the optical module of the soil mapping system shown in FIG. 8.
Figure 10:
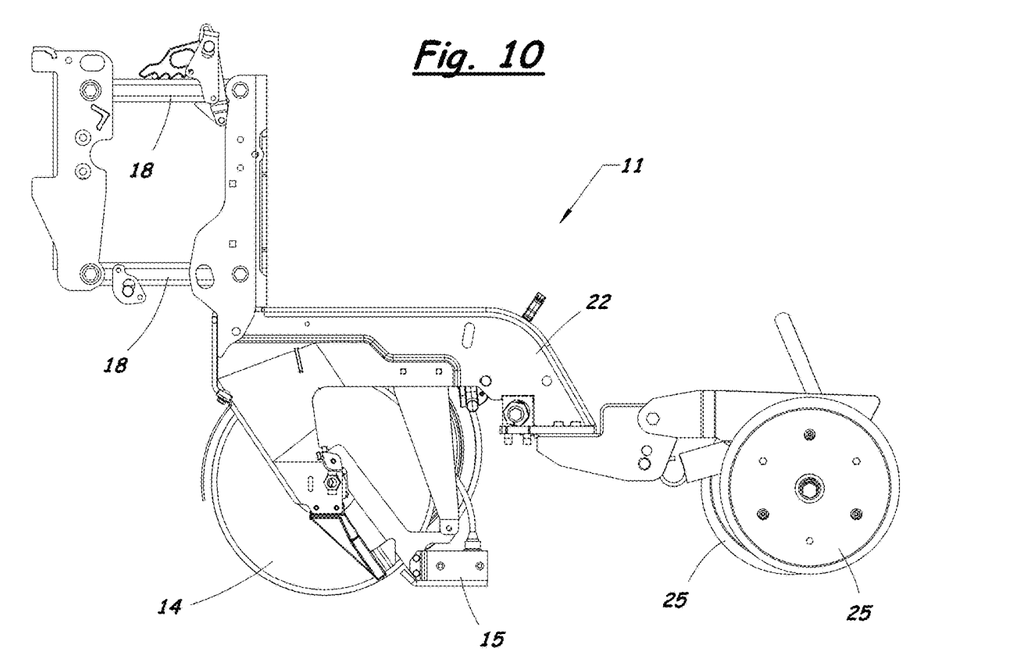
FIG. 10 is an elevation view of the row unit shown in FIG. 9, with the left side gauge wheel and furrow opener disk removed to illustrate the optical module.
Figure 11:
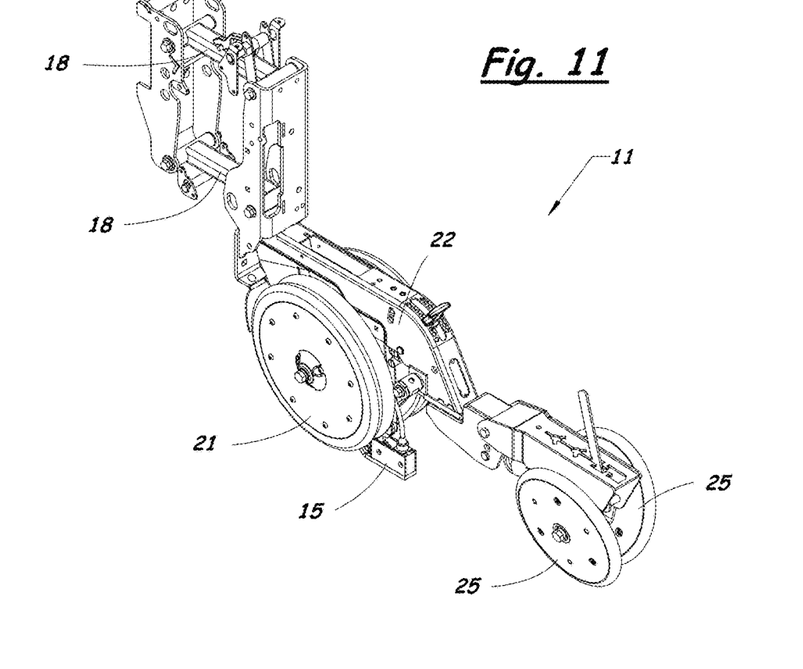
FIG. 11 is a perspective view of the row unit shown in FIG. 9.
Figure 12:
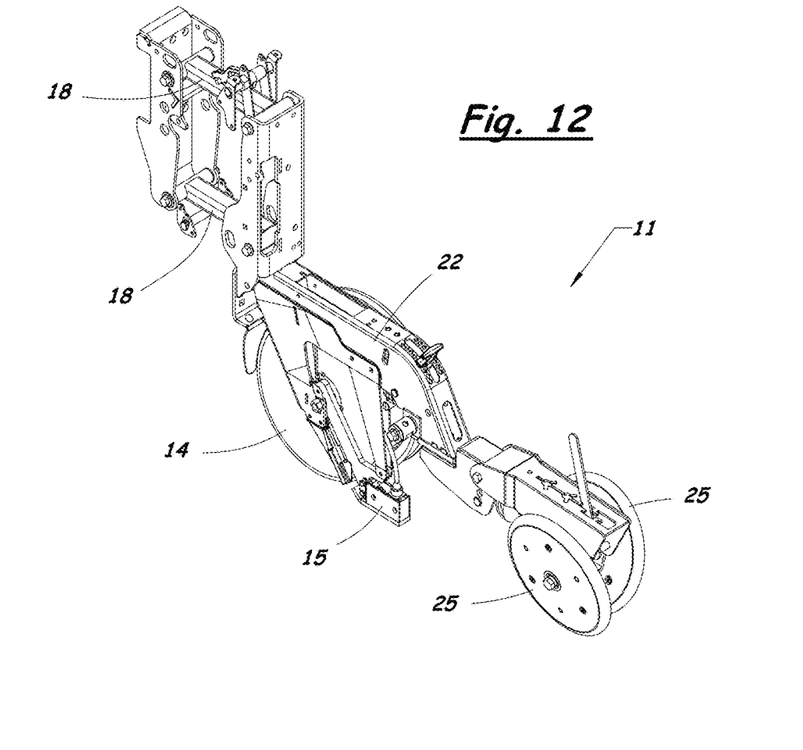
FIG. 12 is a perspective view of the row unit shown in FIG. 11, with the left side gauge wheel and furrow opener disk removed to illustrate the optical module.
Figure 13:
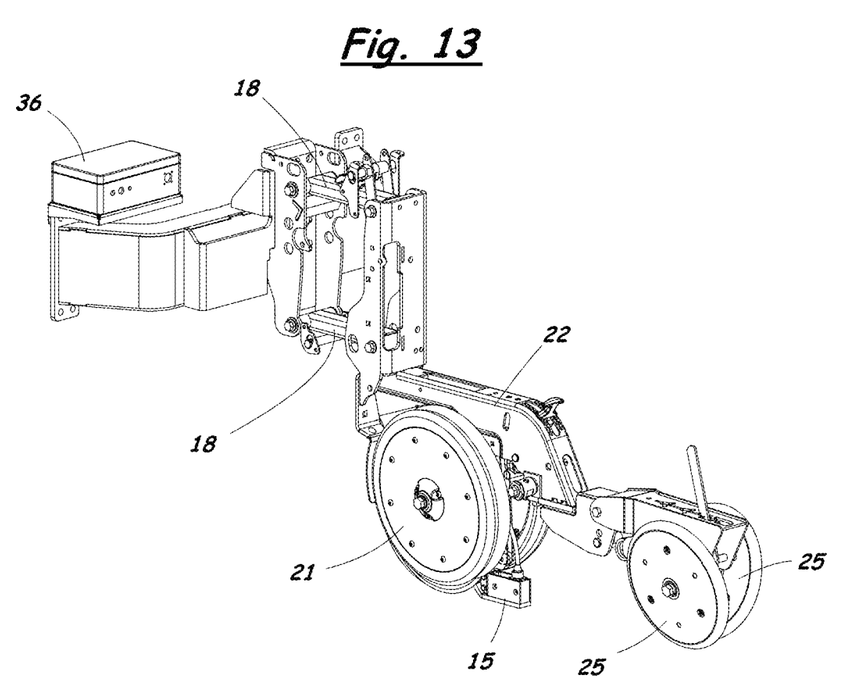
FIG. 13 is a perspective view of the row unit for the soil mapping system shown in FIG. 8, together with the row unit mounting arrangement and controller.

The optical module 11 includes a single photodiode 30, a borosilicate photodiode protection window 31, two different wavelengths of modulating monochromatic light sources 32, 33 modulated at different frequencies, a temperature sensor 34, and a wear plate 35 containing the sapphire window 16 that presses against the soil within the furrow. The modulated light is directed from the two light sources 32, 33 through the sapphire window 16 onto the soil. The reflected light is then received by the photodiode 30, converted to a modulated voltage, and sent to a controller 36. The photodiode 30 is hermetically sealed with the borosilicate window 31 protecting the surface. This allows for easy cleaning, and is robust for outdoor use.

The controller 36 includes two function generators 37 for generating the modulated light from the two light sources 32, 33, a signal conditioning circuit 38 including a phase lock loop (PLL) to separate each source of reflected light from the photodiode signal, an analog to digital (A/D) converter 39, and a serial output 40 for data logging.

The function generators 37 send two separate pulses; one goes to the first wavelength light-emitting diode (LED) 32, the other to the second wavelength LED 33. These pulses are directed at the soil through the sapphire window 16. The light reflected off the soil is read by the photodiode 30 and converted into a modulated voltage. The modulated voltage from the single photodiode 30 is processed through the signal conditioning circuit 38, which converts the modulated voltage to a DC voltage. The DC voltage is processed through the A/D converter 39, then the output is sent through the serial output 40 to the DataLogger or PC 41. The data is georeferenced using a GPS signal from a GPS receiver 42 connected to the DataLogger or PC 41.

By modulating the LEDs 32, 33 at two separate known frequencies and sending the modulated photodiode voltage to the PLL 38, each LED signal can be extracted individually from the photodiode signal, without receiving interference from the other LED light source or ambient light. This allows for a clean signal of only the reflected light of each LED to be stored, free from any outside interference.

Correlating sensor data to soil properties requires the development of calibration equations. Previous calibration attempts with simple optical devices have relied on bivariate regression, with the optical data as the sole sensor variable. One of the situations that can confound optical measurements of organic matter is soil moisture that relates to soil texture variations in addition to relating to organic matter variations.

The present invention includes the use of soil electrical conductivity sensors 43 for collecting electrical conductivity (EC) data in close proximity to the optical module 15. The electrical conductivity sensors 43 include rolling coulters that penetrate the soil and measure the soil EC at a given depth as the implement travels across the field. Soil EC has been proven to correlate well with soil texture. The present invention uses multivariate regression with EC and optical data to help resolve the organic matter variations in the field.

The multivariate analysis is not limited to EC. The present invention also includes the use of an on-the-go soil pH sensor 44 that collects soil pH data as the implement travels across the field, and a GPS receiver 45 that provides elevation signals. Topography derivatives, such as slope, curvature and aspect, contribute to soil moisture variations and can be derived from the elevation signals.

The dual wavelength optical module 15 of the present invention measures how much light is reflected from the soil contacted by the window 16. Darker soils typically have higher organic matter levels, and a simple regression model using lab-analyzed samples with the optical data provides reasonable calibrations. The model may be improved with addition of other sensor data, using multi-variate regression techniques. Organic matter levels vary within a field for a variety of reasons: landscape position, soil textures, and soil pH are key factors affecting organic matter development. Organic matter is formed by decaying plant material, hence areas that produce more biomass have higher organic matter levels as a result. Topography, soil texture and pH are key factors that affect biomass production. For example, most plants don't grow as well on severely sloping ground, or on tight claypan soils, or acidic soils as they do on gentle slopes, loam soils, and balanced pH soils. Soil pH also affects organic matter development with microbial activity—certain soil microbes involved in the breakdown of plant material are inactive when pH is either very high or very low. If the regression model includes topography components such as elevation, slope, and curvature, derived from GPS data, or LIDAR sensors, the model can account for organic matter difference based on landscape position. If the model has soil texture information, such as is available from soil EC sensors, organic matter differences based on textural changes are accounted for. Likewise, if soil pH data such as is available from on-the-go sensing is included, the model can make use of that information. Soil organic matter is a biological property that is related to soil physical properties such as topography and soil texture, and to soil chemical properties such as pH. Additional biological, physical, and chemical property information from sensors and other sources can also be included in the regression models used in the present invention.

An example of a calibration procedure that can be used with the present invention will now be explained. A database of optical, physical, chemical and biological soil information is assembled with Latitude and Longitude. Each data layer (optical, physical, chemical, and biological) is regressed to the soil property target using a leave 1 out validation. The leave 1 out algorithm removes 1 point from the database and uses the remaining points to predict the point removed. The process is repeated until all data points have been predicted. This provides a rigorous method for determining the best unbiased calibration.

After calculating a bivariate regression using each individual data layer, multivariate regression using every data layer combination is also conducted. The results are reported in a table containing metrics such as R-squared (co-efficient of determination) RMSE (root mean square error of the prediction) and RPD (ratio of prediction to deviation); with the best results reported at the top and the poorest at the bottom. The best calibration models are applied to the entire field measurements to provide a prediction for the soil target property.

Unique Features

At least the following features are believed to be unique to the soil mapping system of the present invention:
1. Dual wavelength, economical system with window in firm contact with soil;
2. Mounting on specially configured row unit provides depth control and holds furrow in place during measurement;
3. Single photodiode detector receives both wavelength signals;
4. Used in conjunction with soil EC sensors, elevation sensor, and pH sensor, to improve calibration to specific soil properties;
5. Coulter ahead of unit prepares scene for investigation;
6. Wheels or disks behind system close furrow to prevent erosion; and
7. Multivariate data analysis of optical, EC, elevation, and pH data for soil property calibration.

The present invention provides several advantages over existing soil mapping systems. For example, the depth control and soil scene creation of the present invention are better than the on-the-go spectrophotometer described in U.S. Pat. No. 6,608,672 (Shibusawa) or the spectrophotometer described in U.S. Patent Publication No. 2009-0112475 (Christy et al.).

The cost and complexity of the dual wavelength system of the present invention are much less than on-the-go spectrophotometers described by Shibusawa and Christy et al.

Pressing the window of the optical module of the present invention against the soil provides an advantage over Shibusawa because it allows the window to be self-cleaning.

Devices described in U.S. Pat. No. 5,046,756 (Gaultney) and U.S. Pat. No. 5,038,040 (Funk) did not include use of a window; while the window of the present invention prevents dust and residue from occluding the soil scene. Moreover, Gaultney used only one wavelength; the present invention uses two wavelengths to improve calibration to soil properties.

Various modifications of the mobile soil mapping system of the present invention can be made without departing from the scope of the invention. For example, a window can be mounted on the side of the furrow opener, either at 90° or at the same angle as the furrow. For another example, soil property estimates based on previous soil calibrations can be made on-the-go and displayed on a computer in real-time. For another example, the system can be made to be portable or hand-held.

Other modifications are also possible, including the following: mechanical resistance sensor(s) can be added to the row unit; a soil temperature sensor can be added; a soil moisture sensor can be added; the optical housing can be configured to measure the soil profile; and measurements can be used to control application of seed, fertilizer, or other material in real-time.

While the invention has been described in connection with specific embodiments thereof, it is to be understood that this is by way of illustration and not of limitation, and the scope of the appended claims should be construed as broadly as the prior art will permit.

What is claimed is:

1. A soil mapping system, comprising:
    an implement for traversing a field to be mapped, said implement comprising a frame with a toolbar supported by a frame support wheel, and a row unit pivotally mounted to said toolbar, said row unit comprising a subframe mounted to said toolbar by at least one pivotal linkage member;
    a furrow opener mounted on the subframe for creating a furrow as the implement traverses the field;
    an optical module mounted on the subframe, said optical module comprising at least one light source, a window arranged to press against soil in situ at a predetermined depth within said furrow with consistent pressure to provide a self-cleaning function, and an optical receiver for receiving light reflected back from the soil through the window; and
    at least one depth gauging wheel mounted on the subframe in close proximity to the furrow opener to control the operating depth of the furrow opener and the optical module;
    wherein said at least one light source of said optical module comprises two monochromatic light sources having different wavelengths which are modulated at different frequencies;
    wherein said optical receiver comprises a single photodiode arranged to receive light reflected back from the soil from each of said two monochromatic light sources; and
    further comprising a controller for receiving a modulated voltage from the photodiode, said controller comprising two function generators for sending two separate pulses to the two monochromatic light sources, a phase lock loop to separate each source of reflected light from the photodiode signal to form an output, an analog to digital converter to process the output, and a serial output, wherein the processed output is sent through the serial output for data logging.

2. The soil mapping system according to claim 1, wherein said optical module is arranged to press said window against soil at the bottom of said furrow.

3. The soil mapping system according to claim 1, wherein said furrow opener comprises a pair of rotatable disks arranged on the implement to form a V-shaped slot in the soil.

4. The soil mapping system according to claim 3, wherein said optical module is positioned in the V-shaped slot between said disks.

5. The soil mapping system according to claim 4, wherein said at least one depth gauging wheel comprises a pair of depth gauging side wheels mounted in close proximity to the disks to control the operating depth of the disks and to scrape off soil adhered to an outer surface of the disks.

6. The soil mapping system according to claim 1, further comprising a residue clearing device for removing residue from in front of the furrow opener.

7. The soil mapping system according to claim 6, wherein said residue clearing device comprises a fluted coulter for cutting residue and for opening a slot in the soil in front of the furrow opener.

8. The soil mapping system according to claim 7, wherein said residue clearing device further comprises a pair of trash clearing wheels that clear residue in front of said coulter.

9. The soil mapping system according to claim 1, wherein said at least one pivotal linkage member comprises a parallel linkage that allows the row unit to move vertically relative to said frame to follow ground undulations.

10. The soil mapping system according to claim 9, further comprising a means for adjusting the down-force of the row unit to match soil conditions.

11. The soil mapping system according to claim 1, wherein said row unit further comprises a pair of closing wheels or closing disks following the optical module for closing the slot in the soil to prevent erosion.

12. The soil mapping system according to claim 1, wherein said optical module further comprises a temperature sensor.

13. The soil mapping system according to claim 1, wherein said optical module comprises a wear plate, and wherein said window is a sapphire window contained in said wear plate.

* * * * *